Figure 1:

United States Patent [19]

DeLucas et al.

[11] Patent Number: 5,244,800
[45] Date of Patent: Sep. 14, 1993

[54] CRYSTALS OF HUMAN COMPLEMENT FACTOR D THAT ARE TRICLINIC

[75] Inventors: Lawrence J. DeLucas, Birmingham; John E. Volanakis, Cahaba Heights, both of Ala.

[73] Assignee: The UAB Research Foundation, Birmingham, Ala.

[21] Appl. No.: 514,023

[22] Filed: Apr. 27, 1990

[51] Int. Cl.$^5$ .......................... C12N 9/64; C12N 9/50
[52] U.S. Cl. ..................... 435/226; 435/219
[58] Field of Search ....................... 435/226, 219, 212

[56] References Cited

PUBLICATIONS

Volanakis et al., *Isolation of Complement Protein D . . .* Analytical Biochemistry, 163, pp. 242–246, 1987.
Atkins, *Pysical Chemistry*, Third edition, pp. 550–557, 1986.
Barnum et al., *Quantitation of Complement Factor . . .*, J. of Immunological Methods, 67, pp. 303–309, 1984.
Rosen et al., *Adipsiu and Complement Factor D . . .*, Science, vol. 244, pp. 1483–1487, Jun. 1989.
Niemann et al., *The Use of Monoclonal Antibodies as . . .*, J. of Immunology, vol. 132, No. 2, pp. 809–815, 1984.
Laemmli et al., *Cleavage of Structural Proteins During . . .*, Nature, vol. 227, pp. 680–685, 1970.
Vogt et al., *Mechanisms of Complement Activation . . .*, Molecular Immunology, vol. 22, No. 2, pp. 101–106, 1985.
Giege et al., J. of Crystal Growth, vol. 90, p. 374, 1988.
Einspahv et al., J. of Crystal Growth Crystallization of Recombinant Human I(1B), pp. 180–187, vol. 90, 1988.
Volanakis, J. et al., The New England Journal Of Medicine 312:395–399 (1985).
DeLucas, L. J. and Bugg, C. E., Tibtech, vol. 5:188–192 (Jul. 1987).
DeLucas, L. J. et al., Journal Of Crystal Growth 76:681–693 (1986).
Phipps, D. J. and Aston, W. P., Vet. Immunol. Immunopathol. 19 (3–4):251–258 (1988) (abstract).
Sharf, R. et al., Biochemistry 27 (8):2990–2997 (1988) (abstract).
Takada, A. et al., Complement 4 (2):110 (1987) (abstract).
Chandrashekar R. et al., Exp. Parasitol. 62 (3):362–369 (1986) (abstract).
Pasechnik. V. A., J. Chromatogr. 364P:359–368 (1986) (abstract).
Menger, M. and Aston, W. P., Vet. Immunol. Immunopathol. 7 (3–4):325–336 (1984) (abstract).
Blanchard, D. B. and Leid, R. W., Mol. Immunol. 21 (10):869–876 (1984) (abstract).
Niemann, M. A. et al., J. Immunol. 132 (2):809–815 (1984) (abstract).
Soliakov, L. S. and Kozlov, L. V., Bioorg. Khim. 9 (4):462–469 (1983) (abstract).
Truedsson, L. and Sturfelt, G., J. Immunol. Methods 63 (2) 207–214 (1983) (abstract).
Minta, J. O. and Gee, A. P., Methods Enzymol. 93P:375–408 (1983) (abstract).

*Primary Examiner*—David M. Naff
*Assistant Examiner*—Michael Meller
*Attorney, Agent, or Firm*—Wegner, Cantor, Mueller & Player

[57] ABSTRACT

Crystals of human complement factor D that are triclinic are disclosed. They are made by a method of crystallization known as the "hanging drop" technique. The technique uses 1.0–1400 mM NaCl and polyethylene glycol maintained at a pH of 5.2–7.0, more preferably 5.3–6.1.

2 Claims, 2 Drawing Sheets

FIG.2

CRYSTALS OF HUMAN COMPLEMENT FACTOR D THAT ARE TRICLINIC

The present invention relates to the protein known as complement factor D.

Complement factor D (Enzyme Commission No. 3.4.21.46, *Enzyme Nomenclature,* (1973) American Elsevier, New York) an enzyme of the serine proteinase family, is a protein in human blood that belongs to the group of proteins termed "complement." Complement also includes about 30 additional proteins that act in a concerted fashion to mediate host defenses against invading pathogenic microorganisms.

In order to carry out its host defense function, complement needs to be activated by pathogens. There are two mechanisms for activating complement, the classical and the alternative pathways. The classical pathway becomes activated by antibodies bound to pathogens, whereas the alternative pathway can be activated directly by certain pathogens, thus representing a first line of defense. Complement factor D is necessary for the activation of the alternative pathway. In fact, because complement factor D is the rate limiting enzyme for activation of the alternative pathway, its addition to the blood results in activation of complement through the alternative pathway.

Therefore, complement factor D plays an essential role in the host defenses against invasion by pathological microorganisms, such as bacteria, viruses, fungi, and parasites. Furthermore, under certain pathological conditions, e.g., autoimmune and hypersensitivity diseases, complement activation, including complement factor D, plays an important role in the pathogenesis of tissue damage.

Complement factor D of human origin in a purified form is used as an immunogen to obtain specific antisera needed for the development of ELISA assays. Barnum, et al., *Journal of Immunological Methods,* 67, 303-309 (1984). Solid-phase radioimmunoassay is one means of determining the level of complement factor D in human blood. Volanakis, et al., *The New England Journal of Medicine,* 312, 395-399 (1985).

Accordingly, the present invention provides crystals of complement factor D. The present invention also provides a method of making crystals of complement factor D using vapor diffusion wherein water is extracted from an aqueous solution of complement factor D containing polyethylene glycol and 1 to 4000 mM sodium chloride maintained at a ppH of 5.2-7.0.

Figure 2:
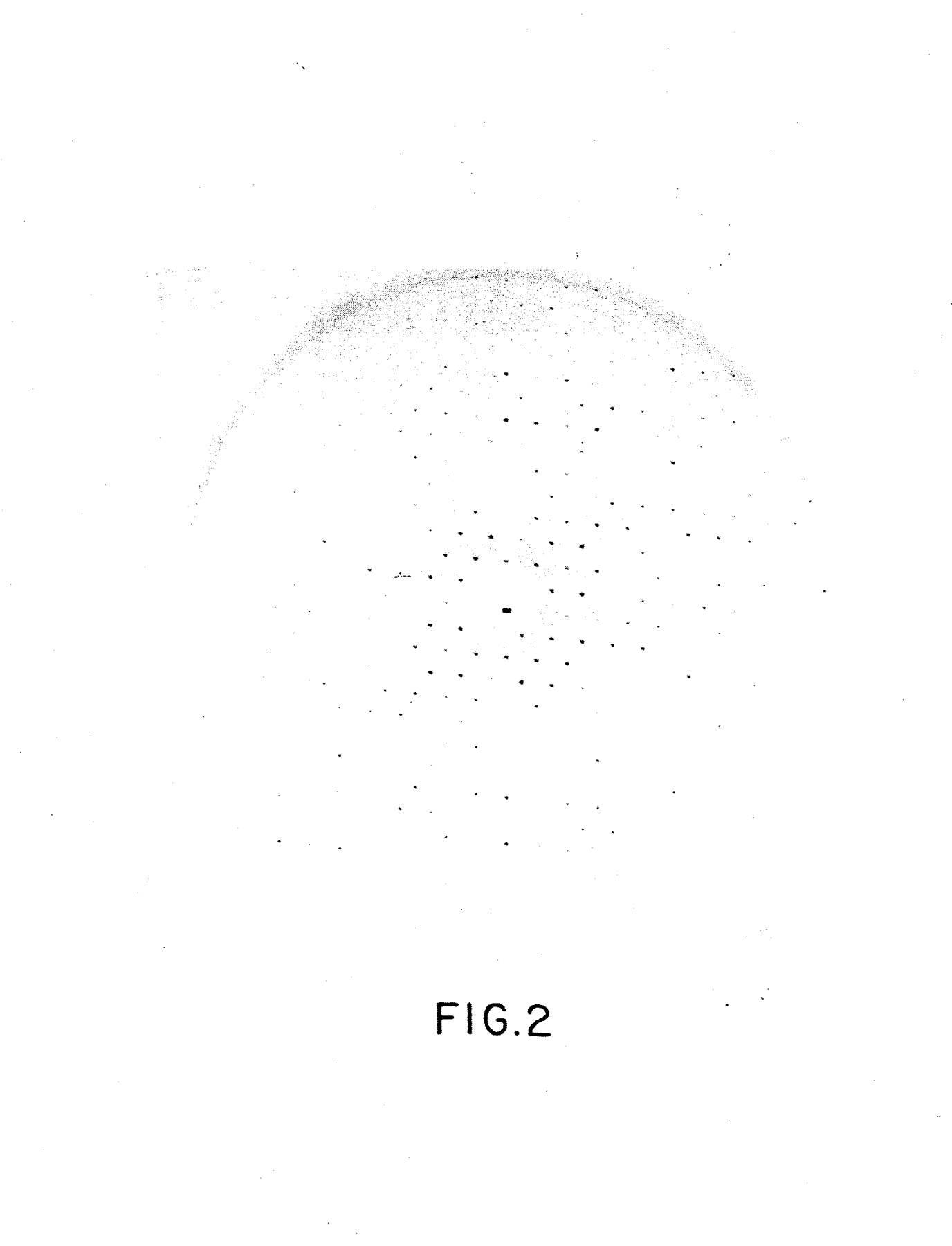

FIG. 1 is a microscopic photograph of crystals of complement factor D grown in accordance with the present invention. FIG. 2 is an X-ray diffraction photograph of crystals of complement factor D grown in accordance with the present invention.

Complement factor D is crystallized in accordance with the present invention by diffusing water through the vapor state from an aqueous solution of liquid complement factor D containing polyethylene glycol (PEG) maintained at a pH of 5.2-7.0, more preferably 5.3-6.1. Preferred crystals are obtained by also including sodium chloride in the aqueous solution. Sodium chloride is believed to facilitate crystallization by increasing the ionic strength of the protein. Concentrations of sodium chloride up to about 4M are suitable, with preferred concentrations of at least about 1 mM, more preferably about 1 mM to 1M.

Preferably, the process of the present invention is carried out using a modification of the vapor-diffusion technique of crystallization. In the preferred process, the aqueous solution is suspended about 1 mm to 20 cm over a material that is more hygroscopic than the aqueous solution in a closed container, which causes water in the form of water vapor to diffuse out of the aqueous protein solution. As the solution equilibrates with the more hygroscopic material through the vapor phase, the protein in the solution crystallizes. The relative amounts of protein, water, and PEG are adjusted so that the protein is almost rendered insoluble in the aqueous solution, such amounts being readily determinable by the skilled artisan. Preferably, the amount of protein is about 3-30 mg/ml of the aqueous solution, more preferably about 10-20 mg/ml. The amount of PEG will also vary slightly depending on its molecular weight; the higher the molecular weight the less is needed to effect the desired result. The molecular weight of the PEG is preferably about 200-40,000. The pH of the solution is preferably maintained by including therein a buffer material that buffers in the desired pH range of 5.2-7.0. Exemplary buffers include 2-(N-morpholino)-ethanesulfonic acid (MES), sodium cacodylate, phosphate buffer, and TRIS buffer, with MES being preferred. Preferred buffer concentrations vary from about 1-50 mM. After addition of a suitable buffer, pH is fine tuned to the desired level using an appropriate acid or base, such as hydrochloric acid or sodium hydroxide. Suitable mediums that are more hygroscopic than the aqueous solution will be readily determinable to those of ordinary skill in the art. Preferably, the hygroscopic material is an aqueous reservoir maintained at the same pH as the aqueous solution. Greater hygroscopicity is preferably attained in the reservoir by providing therein higher concentrations of hygroscopic materials found in the aqueous solution, e.g., by providing a higher concentration (up to a 20-fold increase) of sodium chloride or PEG in the reservoir. The temperature during vapor diffusion is maintained at about 2°-40° C., preferably at about 16°-25° C.

Complement factor D crystals made in accordance with the process of the present invention belong to the triclinic space group and have the following unit cell parameters: a=46.63 Å, b=69.29 Å, and c=40.69 Å; $\alpha$=86.51°, $\beta$=125.87°, and $\gamma$=113.49°. The crystals have a preferable size of at least 0.1 mm³, more preferably at least 0.2 mm³. FIG. 1 shows crystals grown in accordance with the present invention in the suspended droplet in which they are grown. The particular dimensions of the larger crystal shown in FIG. 1 are 0.8×0.5×0.3 mm. The triclinic crystals made in accordance with the present invention facilitate X-ray diffraction studies of complement factor D, which can be used to determine the structure of the protein. FIG. 2 is a 15° precession X-ray photograph of h10 reciprocal lattice planes of crystals of complement factor D grown in accordance with the present invention. Crystal to film distance in the X-ray photograph is 75.0 mm. The X-ray photograph is taken using Ni-filtered CuK$\alpha$ for 20 hours (40 Kv, 100 mA) on a rotating anode X-ray generator. The resolution limit corresponding to typical factor D crystals for the X-ray photograph was observed on a still reflection to be 2.0 angstroms.

In order to more clearly describe the present invention, the following non-limiting examples are provided. In the examples, all parts and percentages are by weight unless indicated otherwise.

EXAMPLE

In this example crystals of complement factor D are made by a vapor diffusion method also known as the "hanging drop" technique. Liquid complement factor D (obtained from Quidel, San Diego, Calif.) is purified as disclosed in Volanakis, et al., *Analytical Biochemistry*, 163, 242-246 (1987). An aqueous solution of the purified factor D and PEG (6000 molecular weight) is prepared and dialyzed against 50 mM MES and 100 mM sodium chloride so that the protein concentration in solution is about 8.5 mg/ml and the amount of PEG is about 8% by total weight of solution to obtain a final pH adjusted to about 5.4 upon addition of NaOH. 300 Samples of the solution, each 2 $\mu$l in volume, are each placed on a glass coverslip coated with an organosilane material (PROSIL-28 obtained from PCR, Inc., Gainsville, Fla.) and inverted such that each sample is suspended about 1.5 cm over an aqueous reservoir of about 1 ml containing 200 mM NaCl, 50 mM MES 300 and about 16% PEG by total weight of the reservoir in a closed container. The samples are allowed to stand suspended over the reservoir for a period of about 48 hours at a temperature of about 22° C. After 48 hours samples containing crystals are aspirated into glass capillary tubes having an external diameter of about 0.5 mm. A glass capillary tube having an external diameter of about 0.2 mm is inserted inside the larger tube until the end of the smaller tube touches the liquid of the sample, which moves away from the crystals into the smaller tube. The smaller tube is then broken off inside the larger tube, the ends of which are then sealed. The isolated crystals are then subjected to X-ray diffraction. The purity of the crystals is measured on SDS Page as disclosed in Laemmli, *Nature*, 227, 680-685 (1970). Upon staining a single band is observed indicating substantially pure (i.e., greater than 99%) and homogeneous (i.e., having identical molecules) complement factor D.

We claim:

1. Crystals of human complement factor D that are triclinic.

2. The crystals of claim 1 having unit cell parameters a=46.63 Å, b=69.29 Å, and c=40.69 Å, $\alpha$=86.51°, $\beta$=125.87°, and $\gamma$=113.49°.

* * * * *